United States Patent [19]
Adams et al.

[11] 3,993,043
[45] Nov. 23, 1976

[54] PORTABLE SLEEP INDUCER

[75] Inventors: Guy Adams, Monroe; Scott D. Goldman, Monsey, both of N.Y.

[73] Assignee: Solitron Devices, Inc., Tappan, N.Y.

[22] Filed: Aug. 21, 1975

[21] Appl. No.: 606,708

[52] U.S. Cl. ............................................ 128/1 C
[51] Int. Cl.² ........................................ A61M 21/00
[58] Field of Search ............... 128/1 C, 1 R, 419 PS, 128/419 R; 330/13, 24, 38 M; 331/78

[56] References Cited
UNITED STATES PATENTS

| | | | |
|---|---|---|---|
| 2,753,453 | 7/1956 | Michels | 331/78 |
| 3,404,235 | 10/1968 | Goldberg | 331/78 |
| 3,609,201 | 9/1971 | Adachi | 331/78 |
| 3,726,285 | 4/1973 | Bowers et al. | 128/422 |
| 3,887,881 | 6/1975 | Hoffmann | 330/13 |

FOREIGN PATENTS OR APPLICATIONS 1,088,607   10/1967   United Kingdom ................ 128/1 C

*Primary Examiner*—William E. Kamm
*Attorney, Agent, or Firm*—Richard G. Geib

[57] ABSTRACT

An analgesic noise generator employs a transistor operated to provide a zener action that is broadcast as the active noise source in an integrated circuit amplifier packaged as a portable unit with means to control tone and volume and enhance life of the power source.

13 Claims, 4 Drawing Figures

3,993,043

PORTABLE SLEEP INDUCER

BACKGROUND

In todays active, mobilized society noise has become a common problem. No where is this felt more than when one is trying to fall asleep. In an effort to aid in sleeping the use of sleeping tablets has mushroomed. As is well known, however, this approach to the problem often creates physical and psychological side effects.

For this reason it was early on considered advantageous to induce sleep by physical methods. One such early method was to use electrodes to apply rectangular pulses. Another development was to create a hypnotic effect with lights, i.e., alternately dimming and brightening of a light source. Recently it has been recognized that white noise broadcast as a hum, for lack of a better worded description, can be quite effective as a sleep inducer. It is to the improvement of such an analgesic noise generator that this invention is directed.

SUMMARY

This invention provides a device, for assisting the induction of natural sleep, which is portable.

As stated above, this invention is concerned with the improvement of analgesic noise generating means. Specifically, the improvement is in using low current drain semiconductor means in a compact package so as to improve life of a power source for the device.

A more detailed object of the invention is to provide a transistorized zener means in combination with a circuit of enhancement type MOS transistors operated by a diode controlled multiple and single power source connection, said diode means preventing power source drain from one of the multiple batteries to the other.

Still another object of this invention is to provide a battery source for portable devices as above that will include a plurality of batteries connected by means to automatically select the highest charged of the batteries and protect the circuitry connected thereto.

DRAWING DESCRIPTION

DETAILED DESCRIPTION

Figure 1:
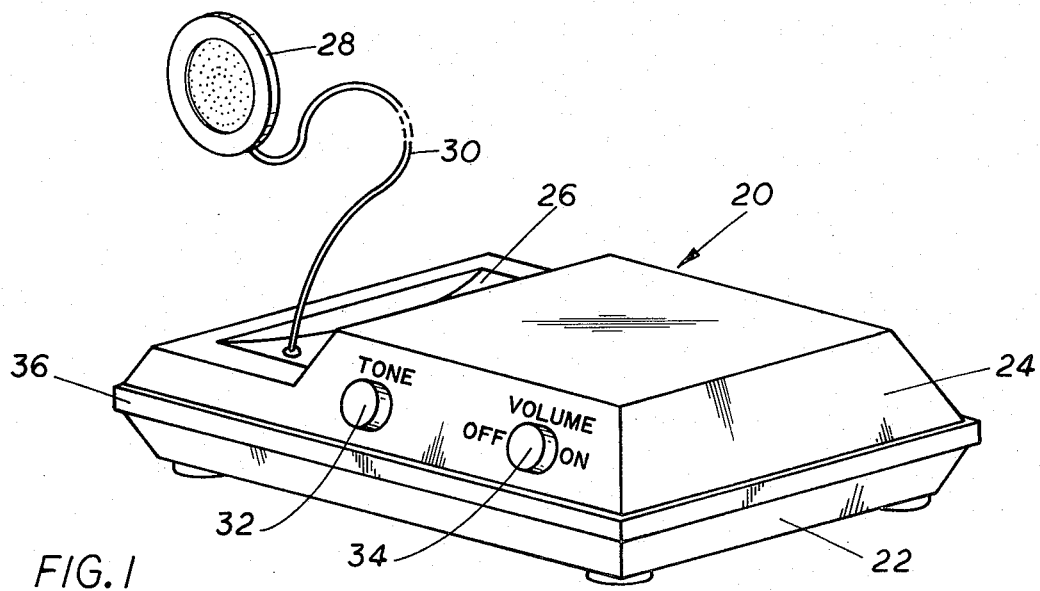
FIG. 1 is an isometric view of the portable sleep inducer unit constructed according to this invention.

With more particular reference now to FIG. 1 there is shown a housing 20 having a base 22 and a cover 24. The cover 24 has formed on one side a pocket 26 for stowage of a speaker 28 and a speaker cord 30. The cover also has, projecting from a front face, tone control knob 32 and volume control 34. In the form shown the cover 24 is attached to base 22 by a flange 36.

Figure 2:
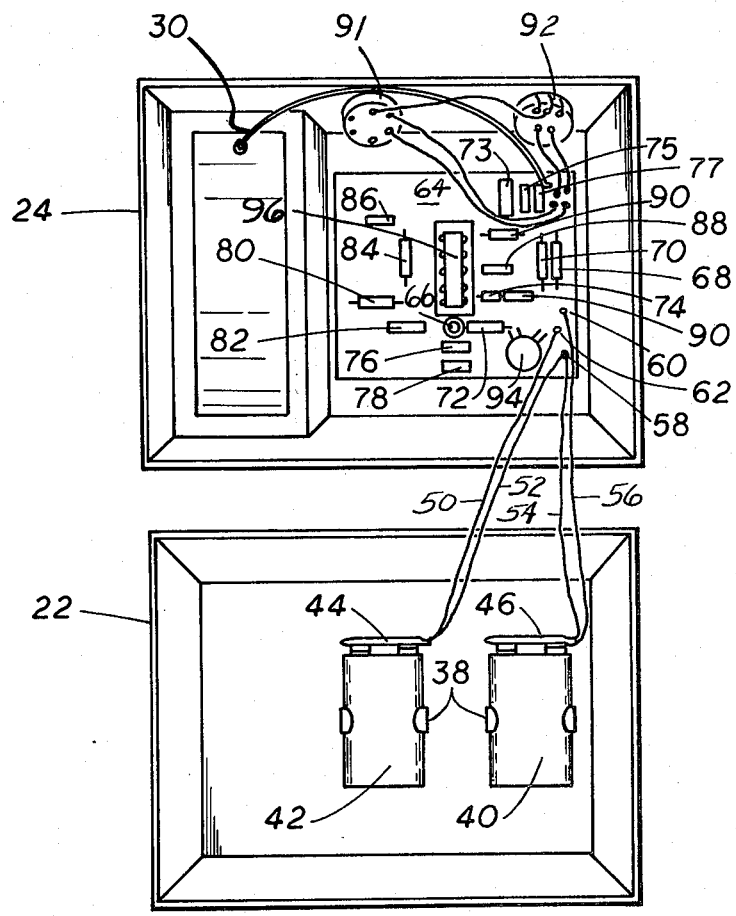
FIG. 2 is a plan view of the interior circuit arrangement within the housing of FIG. 1.

As seen in FIG. 2, the base 22 has a plurality of spring clips 38 for mounting batteries 40 and 42. It should be noted that although two batteries are shown, there could be more used for additional fail-safe and lifetime provisioning as will appear hereinafter. The batteries shown are of the usual nine volt variety common to transistor radios with cap connectors 44 and 46 for leads 50, 52 and 54, 56.

Cover 24 has input connections 58, 60 and 62 to provide a common ground, as at 58 and separate positive inputs as at 60 and 62 to a printed circuit board 64 bonded to the cover 24 with its discrete components projecting therefrom for easy service without removal of the board 64 being necessary.

More particularly, there is mounted to the board 64 an PNP transistor 66, germanium diodes 68 and 70, capacitors 72, 73, 74, 75, 76, 77, 78, 80 and 82 and resistors 84, 86 and 88. The cover mounts switch 91 and pot 92 under the face for knobs 32 and 34. The structure is completed by an IC clip 96.

Diodes 68 and 70 in addition to preventing drain of any battery through another also act to preclude the connection in reverse of the batteries from affecting the circuitry powered by same.

Figure 3:
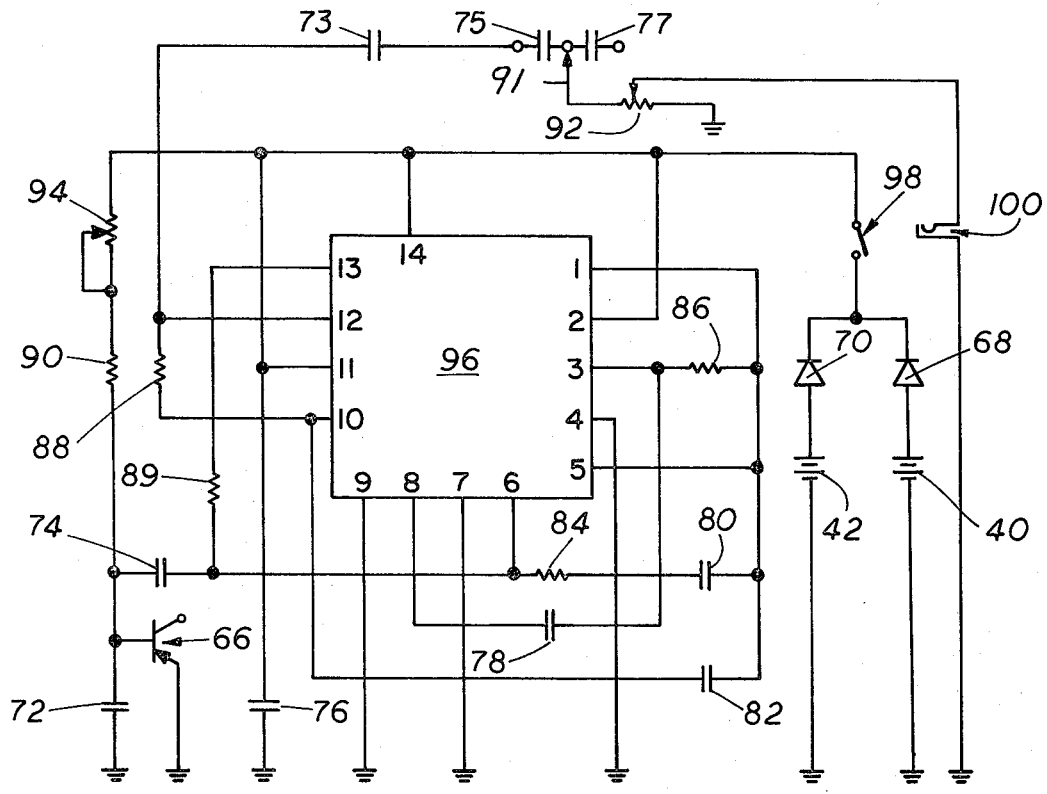
FIG. 3 is a circuit diagram of the analgesic noise circuit of FIG. 2.
Figure 4:
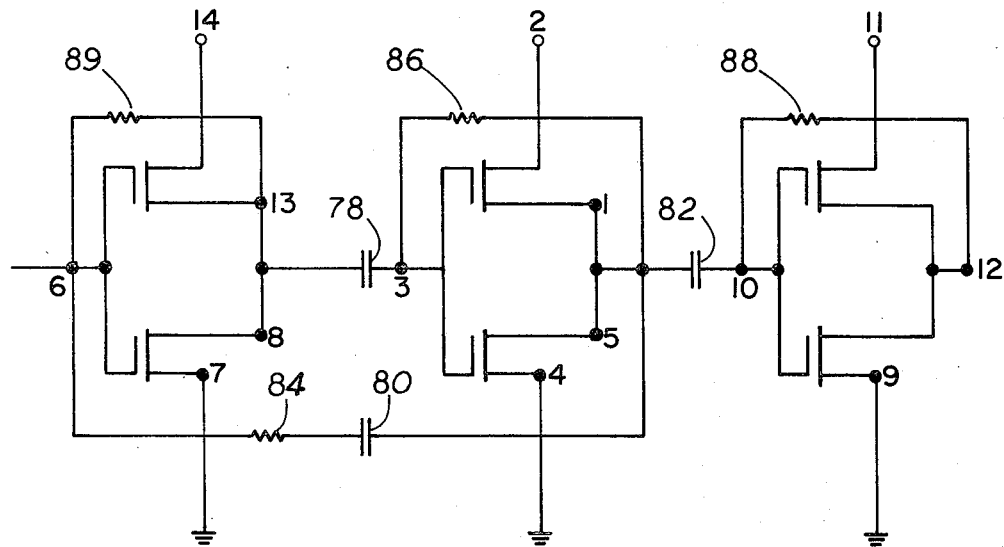
FIG. 4 is a circuit diagram of a portion of the circuit of FIG. 3 showing the internal structure of the IC chip thereof in more detail.

The manner of connection of the batteries and the above discrete devices via a PC Board 64 is better shown by FIG. 3. As seen therein the IC chip, a Solitron CM 4007 as typical, is used having fourteen points of connections labeled as pins 1 through 14 whose input is pin 6 and whose output is pin 12. This is more particularly shown by FIG. 4 wherein the chip has three N-channel and three P-channel enhancement type MOS transistors between pins 6 and 12 connected in series by capacitors 78 and 82, each one of a set being connected via a minor feedback loop comprising resistors 89, 86 and 88 to bias the IC in a linear mode. In addition, a major feedback circuit comprised of resistor 84 and capacitor 80 is provided across the first two of the three to eliminate high frequency noise and allow more power in the audio range.

The circuit of FIG. 3 shows also the manner of connection of diodes 68 and 70 to positive outputs of batteries 40 and 42. The outputs of these diodes is joined at switch 98, a part, with pot 92, of the volume control under control of knob 34. Also, as seen by FIG. 3 knob 32 controls switching in capacitors 73, 75 and 77 in providing tone control to speaker jack 100.

OPERATION

In operation when switch 98 is turned on to permit current flows to pot 94 by being passed by one or both diodes 68 and 70, which is determined by the level of charge of batteries 40 and 42, i.e., if one is greater than the other than the diode of the other will be blocked from passing current as well as be prevented from shorting to the other, lower charge producing, battery. Pot 94 adjusts the current flow to PNP transistor 66 via resistor 90, whose emitter is grounded, to thereby adjustably control the reverse conduction of transistor 66 to establish a noise frequency therefrom by zener action thereof. Capacitor 72 by its cornering actions cuts off the frequency to that desired, whereas capacitor 74 feeds the frequency to the input pin 6 of the IC while blocking DC therefrom.

The IC by its nature is power conservative. However, in order to further conserve power to only that needed to produce a broadcast of the analgesic noise, the IC has the three minor feedback circuits to bias the IC in the linear mode to hold the output to approximately one-half voltage, and a major feedback circuit to optimize power in the audio range while eliminating the need for excess power by curtailing the high frequency range beyond that of the audio range.

A hum or waterfall sound is then broadcast via pin 12 to capacitor 73 to refine the tone which can be further refined by pot 92 switching in or out one or both of capacitors 75 and 77.

Having described an operative construction of the invention the claims therefore are set forth as follows:

1. Means to produce and broadcast analgesic noise, said means comprising:
   a switchable source of electrical energy supply having a plurality of battery means with a common connection to one terminal of each and means to connect the other terminal of each to one of a plurality semiconductors equal to the number of batteries so as to control the providing of a necessary amount of energy from one or more portions of the parallel supply to a switch;
   a circuit connected to said source, said circuit including, a semiconductor connected to said source so as to establish a Zener action therein whereby noise frequencies are created,
   a means to limit the frequency spectrum of said semiconductor,
   a CMOS circuit connected to said source and to said semiconductor and constructed with minor and major feedback means to function as a low power requirement amplifier for the output of the means to limit frequency spectrum; and,
   speaker means with variable signal control means connected to said circuit to control the comfort level of the analgesic noise from the speaker means.

2. The means of claim 1 wherein said semiconductor is a PNP transistor whose emitter is grounded via the common connection to one terminal of each battery means and whose base is connected to said source via said switch.

3. The structure of claim 2 wherein said means to limit the frequency spectrum is a cornering circuit between said common connection for said source and said base, said cornering circuit comprising a capacitor.

4. The structure of claim 3 wherein said CMOS circuit is connected to the base of said PNP transistor.

5. The analgesic device of claim 3 wherein said CMOS circuit connected to said PNP transistor is connected by a capacitor to block DC from said source.

6. The analgesic device of claim 5 wherein the CMOS circuit may be characterized as including three N channel and three P channel enhancement type MOS transistors arranged in successive stages with the minor feedback being a resistance circuit about the output and input of each and the major feedback being between the output of one stage and the input of another, an input stage.

7. The structure of claim 1 wherein said CMOS circuit connected to said semiconductor is by means of a device to block DC from said source.

8. The analgesic device of claim 1 wherein the CMOS circuit may be characterized as including three N channel and three P channel enhancement type MOS transistors arranged in successive stages with the minor feedback being a resistive circuit about the output and input of each and the major feedback being between the output of one stage and the input of another, an input stage.

9. The structure of claim 1 wherein said switchable source is arranged as a parallel supply of electrical energy characterized by multiple batteries having their ground potential in a common ground connection with said circuit and their positive potential having a separate connection from each being to separate diode means from which the supply is joined in parallel to said switch means.

10. An analgesic device comprising:
    a housing having a pocket;
    a speaker stowable in the pocket and extendable therefrom;
    a means to produce analgesic sound including a semiconductor noise source and an integrated circuit amplifier characterized by N channel and P channel enhancement type MOS transistors;
    a means to control sound from said integrated circuit;
    a means to broadcast sound over said speaker; and,
    a source of electrical energy for said means to produce analgesic sound.

11. The device of claim 10 wherein the means to produce analgesic sound comprises a subassembly where a PNP transistor has its emitter grounded and its base connected to a lead between a resistance means and a capacitor connection to ground which lead is tapped by a capacitive connection leading to a resistance and another by a capacitive connection leading to a resistance and another lead joined with the integrated circuit on a PC board attached to the housing.

12. The device of claim 10 wherein said source is a plurality of batteries connected in parallel by diode means to self select one or all to be the source.

13. The device of claim 11 wherein the source is a plurality of batteries connected in parallel by diode means that will self select one or all to be the source to the resistance means.

* * * * *